US005637499A

United States Patent [19]
Turick

[11] Patent Number: 5,637,499
[45] Date of Patent: Jun. 10, 1997

[54] METHOD FOR ENHANCING MICROBIAL UTILIZATION RATES OF GASES USING PERFLUOROCARBONS

[75] Inventor: Charles E. Turick, Idaho Falls, Id.

[73] Assignee: Lockheed Idaho Technologies Company, Idaho Falls, Id.

[21] Appl. No.: 544,219

[22] Filed: Oct. 17, 1995

Related U.S. Application Data

[63] Continuation-in-part of Ser. No. 235,815, Apr. 29, 1994, abandoned.

[51] Int. Cl.$^6$ .......................... B01D 53/34; B01D 53/56; C12N 1/38; C12N 1/20
[52] U.S. Cl. ..................... 435/266; 435/244; 435/253.3; 55/244
[58] Field of Search .......................... 435/266, 244, 435/253.3; 55/244

[56] References Cited

U.S. PATENT DOCUMENTS

| | | | |
|---|---|---|---|
| 4,166,006 | 8/1979 | Hertl et al. | 435/244 |
| 5,180,676 | 1/1993 | Ichikawa et al. | 435/240.1 |
| 5,268,298 | 12/1993 | Fike et al. | 435/284 |

OTHER PUBLICATIONS

Rols et al. "Mechanism of Enhanced Oxygen Transfer in Fermentation Using Emulsified Oxygen–Vectors." Biotechnology and Bioengineering, vol. 35, pp. 427–435. 1990.

Yamamoto et al. "Enhancement of Autotrophic Growth Rate of Alcaligenes Eutrophus in a Medium Containing Perfluorcarbon Under Low Oxygen Partial Pressure." Biotechnology Letters, vol. 14, No. 8, pp. 733–736. Aug. 1992.

King et al. "Perfluorocarbons and Cell Culture." Bio/Technology, vol. 7, pp. 1037–1042. Oct. 1989.

Sargeant et al. "Properties of perfluorinated liquids." Federation Proceedings, vol. 29, No. 5, pp. 1699–1703. Sep. 1970.

Primary Examiner—Esther M. Kepplinger
Assistant Examiner—T. J. Reardon
Attorney, Agent, or Firm—Alan D. Kirsch

[57] ABSTRACT

A method of enhancing the bacterial reduction of industrial gases using perfluorocarbons (PFCs) is disclosed. Because perfluorocarbons (PFCs) allow for a much greater solubility of gases than water does, PFCs have the potential to deliver gases in higher concentrations to microorganisms when used as an additive to microbial growth media thereby increasing the rate of the industrial gas conversion to economically viable chemicals and gases.

18 Claims, 2 Drawing Sheets

METHOD FOR ENHANCING MICROBIAL UTILIZATION RATES OF GASES USING PERFLUOROCARBONS

CONTRACTUAL ORIGIN OF THE INVENTION

The United States Government has rights in this invention pursuant to Contract No. DE-AC07-76ID01570 between the United States Department of Energy and EG&G Idaho, Inc., now Contract No. DE-AC07-94ID13223 between Lockheed Idaho Technologies Company and the United States Department of Energy.

This is a continuation-in-part application of application Ser. No. 08/235,815 filed Apr. 29, 1994 now abandoned.

TECHNICAL FIELD

A method is disclosed to increase the solubility of gases such as industrial gases e.g., carbon dioxide, nitrogen, nitrogen oxides, carbon monoxide, etc.); hydrocarbon vapors (e.g., methane, hexane, butane, propane, phenols and chlorinated hydrocarbons); and volatile organic compounds (e.g., benzene, toluene, ethylbenzene and xylene) and other industrial gases in biological growth media using vectors (carriers) such as perfluorocarbons and perfluorocarbon emulsions as an additive to increase the mass transport of gases and vapors to organisms metabolizing in the growth medium, for the purpose of allowing the organisms to utilize the gases and vapors as a carbon source, electron donor, or electron acceptor.

Industrial gases, hydrocarbon vapors and volatile organic compounds are often considered pollution problems and need to be converted to either environmentally benign compounds or economically viable products. The potential exists for industrial bioprocesses to utilize these gases or vapors for environmental control or chemical production. The limiting factor in the bioprocessing of these compounds is their low solubility in biological growth media. Because gases dissolve in perfluorocarbons in higher concentrations than in aqueous media, the addition of perfluorocarbons (PFCs) into the growth media contacting gases of interest increases the solubility of gases into the growth media. Gas solubility in PFCs follows Henry's law. Gas laden PFCs contacting microorganisms in the growth media increase the transfer of gases to the microorganisms and thereby increase the metabolic rates of the microorganisms. By emulsifying the PFCs, the surface area is increased allowing for increased contact with microorganisms and an even greater rate improvement. The smaller and more stable a PFC emulsion, the greater the utility in a bioprocess.

In addition, hydrocarbons and volatile organic compounds also have an increased solubility in PFCs of like structure, for example, hexane is soluble in perfluorohexane and benzene is soluble in perfluorobenzene. The utilization of PFCs in the manner mentioned above will also increase the rate of hydrocarbon, and volatile organic compounds degradation in a bioprocess.

The disclosure presented here demonstrates the use of perfluorocarbon emulsions in an anaerobic environment to increase microbial growth and gas utilization relative to conventional methods, however it should be understood that any gas that follows Henry's Law is capable of being utilized in the subject invention.

BACKGROUND OF THE INVENTION

Nitrogen oxides ($NO_x$) are gaseous emissions from numerous industrial process, such as fossil fuel combustion, pulp and paper manufacturing, and pharmaceutical production. Upon release into the atmosphere, $NO_x$ compounds have demonstrated various deleterious effects including the production of acid rain and stratospheric ozone damage. Nitric oxide (NO) and nitrogen dioxide ($NO_2$) are the two most common forms of $NO_x$. Nitrous oxide ($N_2O$), another form of $NO_x$, is not as abundant from combustion sources but has a significant impact on the greenhouse effect, contributing to 5% of global warming due to its long residence time (>150 years) in the atmosphere. $N_2O$ has also been shown to increase in concentration from fluidized bed boilers as well as from $NO_x$ reburners.

$NO_x$ gases, from industrial sources, have the potential of being converted, via anaerobic bioprocessing, to diatomic nitrogen ($N_2$), an environmentally benign compound. Bioprocessing of $NO_x$ compounds, using naturally occurring nitrate-reducing bacteria, have been demonstrated to effectively convert $NO_x$ to diatomic nitrogen ($N_2$), with gas solubility being the limiting factor.

Perfluorocarbons are hydrocarbons with fluorine substituted for hydrogen. These chemicals allow for increased gas solubility, are chemically inert, and have not been demonstrated to be biodegradable or been shown to be toxic to microorganisms.

Perfluorocarbons have received little attention in industrial microbiology for anaerobic bioprocesses or hydrocarbon or volatile organic compounds degradation. This invention demonstrates the potential for the use of perfluorocarbon emulsions in the bioprocessing of industrially important gases, hydrocarbons and volatile organic compounds. Perfluorocarbons are colorless, dense, nontoxic liquids having very low surface energies and consist of a ring or straight chain hydrocarbon in which hydrogen atoms have been replaced by fluorine atoms. Examples are: perfluorodecalin, perfluorohexane, perfluoropentane, and perfluorobenzene.

Nitrous oxide ($N_2O$) was chosen as a model $NO_x$ compound, primarily because all $NO_x$ compounds entering a bioprocess must first be reduced to $N_2O$ prior to reduction to $N_2$. Perfluorocarbon emulsions were employed to increase $N_2O$ transfer in anaerobic, aqueous growth media in order to facilitate gas transfer to pure cultures of bacteria.

SUMMARY OF THE INVENTION

This invention provides a method to deliver gases or vapors in increased concentrations (relative to the surrounding gas and hydrocarbon concentrations in the gas or aqueous phases in a bioreactor) to microorganisms using these gases or vapors for growth in a bioreactor. The increase in solubility of a gas or gases, such as industrial gases (i.e., carbon dioxide ($CO_2$), nitrogen ($N_2$), nitrogen oxides ($N_2O$, NO), carbon monoxide (CO), etc.); hydrocarbons vapors (e.g., methane, hexane, butane, propane, phenols and chlorinated hydrocarbons); and volatile organic compounds (e.g., benzene, toluene, ethylbenzene and xylene) in a biological growth medium is accomplished by using vectors such as perfluorochemical emulsions as an additive to the medium. The vectors demonstrate increased solubility of many gases and vapors due to their chemical nature but do not bond tightly to the gases or vapors and thereby release them easily for use by microorganisms. The gases or vapors are dissolved into vectors whereby the gases or vapors are carried in greater concentration to microorganisms than in the gas or aqueous phases of the bioreactor. The vectors have a higher concentration of gases or vapors dissolved in them and, therefore, can increase the rate of transport of gases or vapors to microorganisms. The increased concentration of gases or vapors can increase the growth rates of metabolizing organisms in the growth medium thereby increasing the productivity and efficiency of the bioreactor.

The invention consists of a method for enhancing microbial utilizations of industrial gases, hydrocarbons or volatile organic compounds, using perfluorocarbon (PFC) emulsions, the method comprising:

a. providing a sterile PFC solution;

b. mixing the PFC solution with a biological growth medium and a surfactant, the biological growth medium being suitable to support microbes capable of metabolically utilizing the industrial gas and the surfactant capable of being emulsified;

c. emulsifying the biological growth medium, PFC solution, and surfactant mixture by circulation in a high-pressure emulsifier so that the PFC is in the distributed state throughout the emulsified biological growth medium;

d. adding the emulsified biological growth medium, PFC solution, and surfactant mixture to a bioreactor containing microbes capable of metabolically utilizing the industrial gas;

e. aseptically adding the gas to the bioreactor containing emulsified growth medium, PFC solution, and surfactant mixture; and f. controlling a temperature and agitation rate of the growth medium and microbes within the bioreactor to maintain conditions sufficient for microbial activity, thereby increasing the consumption rate of the gas by the microbes by increasing the solubility of the gas and a gas transfer rate to the microbes.

Other objects, advantages, and capabilities of the present invention will become more apparent as the description proceeds.

DETAILED DESCRIPTION OF THE INVENTION

Figure 1:
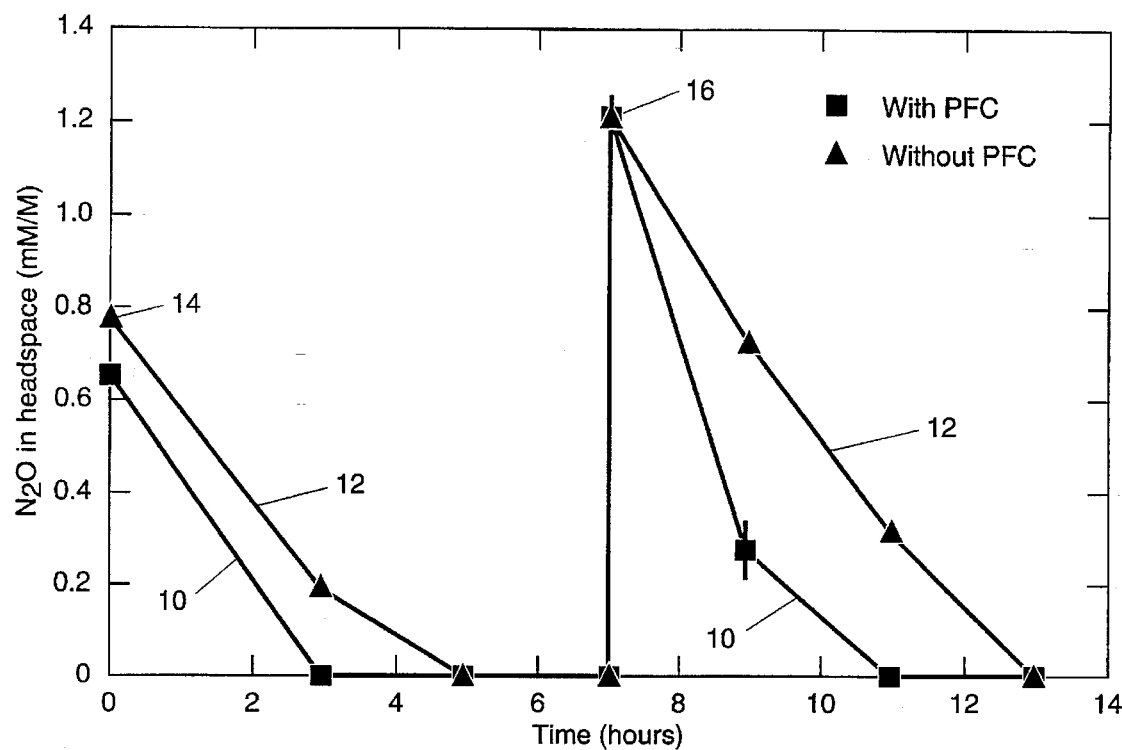
FIG. 1 is a graph of nitrous oxide ($N_2O$) reduction versus time in an experiment with PFC in the carrier and without PFC in the carrier.

The main objective of this invention is to attempt to increase and optimize gas concentration in liquid microbiological media using perfluorocarbons (PFCs). PFCs bind reversibly to gases and volatile compounds, increasing their solubility relative to that of water. Examples of PFCs capable of being utilized in the present invention include, but are not limited to, perfluorobutane, perfluoropentane, perfluorohexane, perfluoroheptane, perfluorooctane, perfluorononane, perflourocyclobutane, perfluorocyclopentane, perfluorocyclohexane, perfluoromethylcyclohexane, perfluorodimethylcyclohexane, perfluoroethylcyclopentane, perfluorbenzene and perfluorotoluene, and mixtures thereof.

Experiments

Since enhanced mass transfer with PFCs occurs when they first contact the gases in the headspace and transfer the gases to bacteria, contact with the bacteria increases the mass transfer rate. Therefore, in order to increase physical contact with headspace and bacteria, PFCs were emulsified, thereby increasing their surface area and keeping them in suspension for a longer period of time than nonemulsified PFCs.

Sterile PFC emulsions were made by first gassing out PFCs with helium (He) and then sterilizing the PFCs. A sterile solution of Tryptic Soy Broth (TSB) by DIFCO and the surfactant (Pluronic F68™ a block polymer of polyoxyethylene and polyoxypropylene by BASF-Wyandotte Corp.) was made (2.1 g Pluronic F68 in 100 mL of Tryptic Soy Broth). Other anionic and nonionic surfactants (detergents) can also be used in the present invention, such as, sodium lauryl sulfate, monolaurate (Tween 20), monooleate (Tween 80), polyoxyethylene, polyoxypropylene, polyoxyethylenesorbitan and block polymers. Fifteen (15) mLs of a sterile PFC was added to 30 mLs of the TSB and Pluronic F68 solution. The mixture was added to a high-pressure emulsifier and circulated several times for emulsion production. The emulsion sizes ranged from 7.1–95.7 nanometers in diameter with an average of 17.8 nanometers.

Growth and gas utilization rate experiments were conducted using perfluoropentane (a 3M Industrial Chemical Products Division designated as FC 77) in the emulsified form with $N_2O$ as the terminal electron acceptor for *Pseudomonas denitrificans*. The medium used was Tryptic Soy Broth (TSB) and a dense bacterial inoculum was added. Spectrophotometric analysis for growth was accomplished by separating the PFC emulsion from the bacteria by centrifugation at low speed. After the first 7 hours of growth, a second addition of $N_2O$ was added to the serum bottles. Results demonstrated increased rates of gas utilization by the bacteria with PFC emulsions present in the medium relative to controls.

These batch analyses suggest that PFCs significantly increase gas transfer rates to bacteria and, therefore, increase the rates of gas utilization. Furthermore, volatile hydrocarbons, such as those found in gasoline, are also soluble in many PFCs due to their chemical similarity. These chemicals which are minimally soluble in water and, therefore, difficult to degrade microbially may demonstrate more rapid degradation in the presence of PFCs.

Addition of PFCs to bioreactors has the potential to improve gas mass transfer kinetics and increase reactor efficiency.

Experimental Results and Discussion

Referring now to TABLE 1 and FIG. 1, serum bottles containing perfluorocarbon emulsions demonstrated a more rapid rate of $N_2O$ utilization at 10 than controls at 12 with no perfluorocarbons after the initial $N_2O$ addition at 14 as well as after the second addition of $N_2O$ at 16 in the serum bottle headspace. Since the $N_2O$ added to the headspace was essentially the only $NO_x$ compound present in the TSB medium for bacterial utilization as a terminal electron acceptor, gas solubility was the only limiting growth factor.

TABLE 1

| | Rates of $N_2O$ Reduction ($Hr^{-1}$) | |
|---|---|---|
| | With PFC | No PFC |
| 1st $N_2O$ Addition | 1.40 | 0.52 |
| 2nd $N_2O$ Addition | 0.79 | 0.34 |

Figure 2:
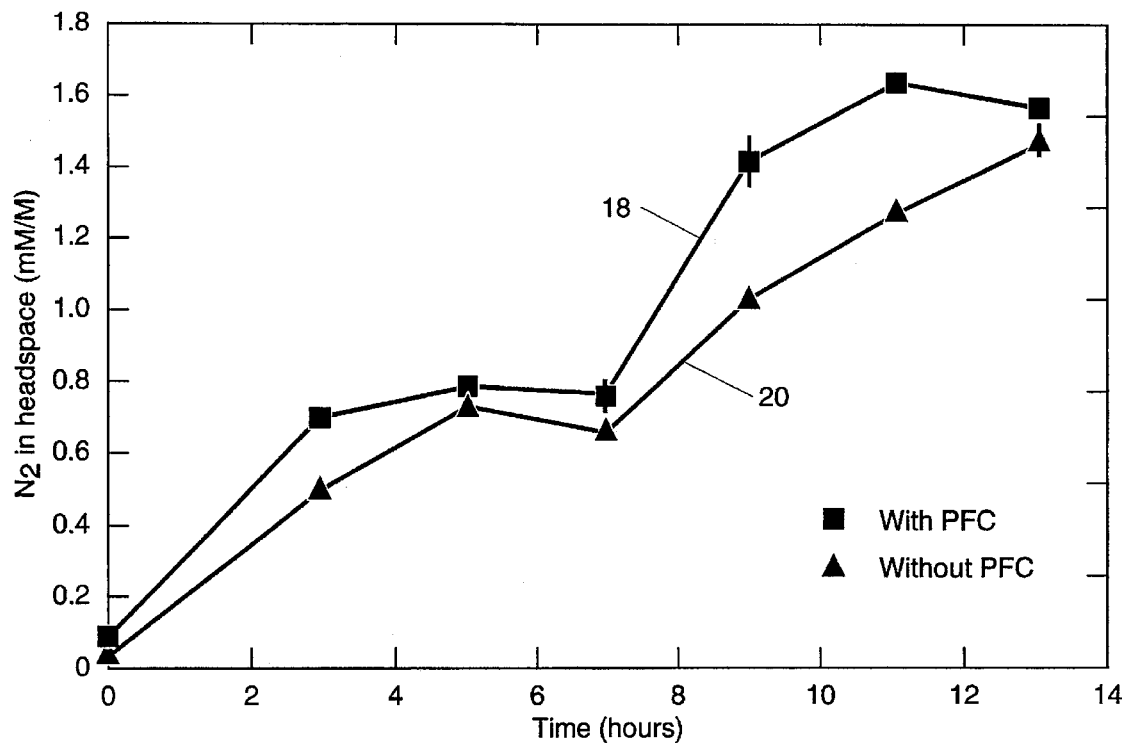
FIG. 2 is a graph of nitrogen ($N_2$) evolution versus time in the above experiment.

Bacterial reduction of $N_2O$ occurred as evidenced by the evolution of $N_2$ in the headspace (TABLE 2 and FIG. 2).

Similarly, $N_2$ concentrations increased as $N_2O$ concentrations declined in the headspace. The increased rates of $N_2O$ reduction and $N_2$ evolution at 18 observed in cultures containing perfluorocarbons demonstrates the utility of using perfluorocarbons to increase the rate of gas exchange in bioprocess.

TABLE 2

| | Rates of $N_2$ Generation $(Hr^{-1})$ | |
|---|---|---|
| | With PFC | No PFC |
| 1st $N_2O$ Addition | 0.76 | 0.39 |
| 2nd $N_2O$ Addition | 0.78 | 0.20 |

Evolution of $N_2$ from media was a result of $N_2O$ reduction by the bacteria and demonstrated increased rates of evolution from liquid cultures containing perfluorocarbon emulsions compared to cultures without perfluorocarbon emulsions 20 (FIG. 2). The rates of $N_2$ evolution were also doubled due to the presence of perfluorocarbons (TABLE 2).

Figure 3:
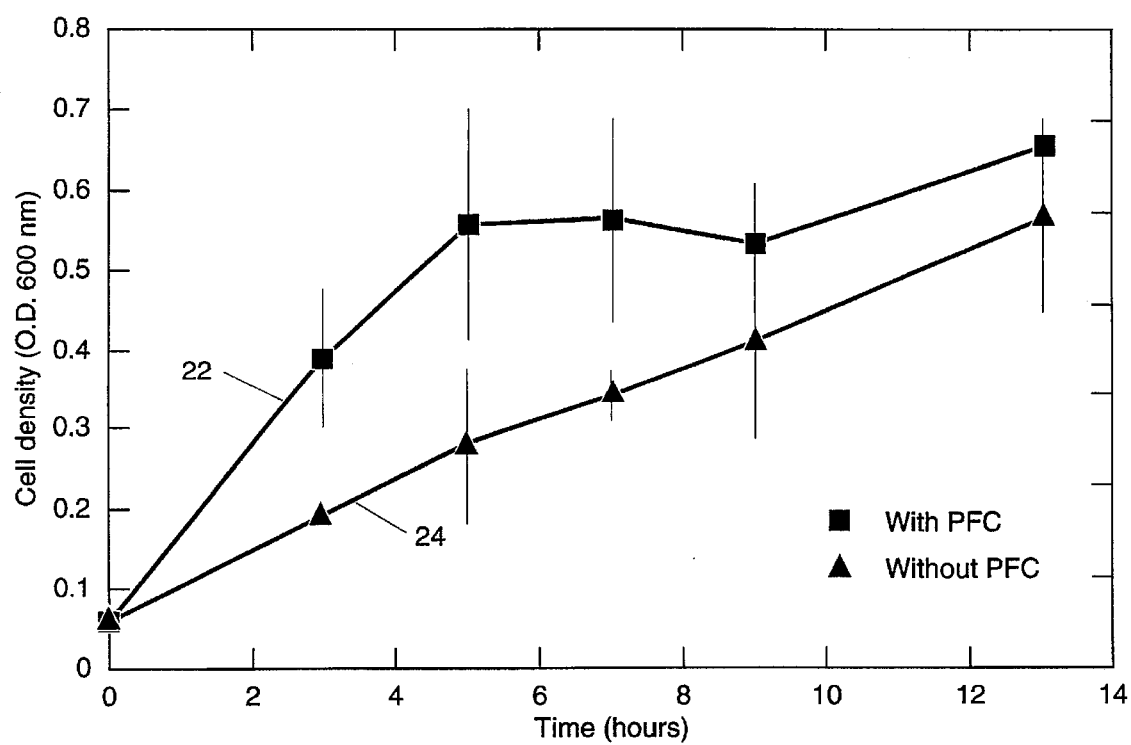
FIG. 3 is a graph of microbial growth (cell density) versus time in the above experiment.

Bacterial growth measured as cell density was correspondingly enhanced in the presence of PFC emulsions at 22 (FIG. 3) relative to controls at 24. The bacteria in contact with the PFCs demonstrated rapid growth which appeared to level off after 7 hours. Bacteria not exposed to PFCs displayed consistent growth throughout the experiments (FIG. 3). The cause of the decreased growth rate of PFC exposed bacteria is not immediately evident. Since this work was performed in batch, growth may have been restricted due to more rapid increases of bacterial metabolites in the medium or bacterial adherence to the PFC emulsions may have caused an underestimation of bacterial numbers with time.

The procedural steps in this method consisted of:
1. outgassing the PFC using a helium gas flow over an iced serum vial containing PFC;
2. sterilizing the serum vial with PFC at 120° C. and 15 psi for 20–30 minutes;
3. adding the PFC to a sterile emulsion growth medium such as TSB so that the PFC is in the distributed state throughout the emulsion;
4. aseptically adding the industrial gas with helium, as the balance gas, to the growth medium;
5. adding bacteria such as *Pseudomonas denitrificans*;
6. incubating the growth medium at 100 rpm at 35° C.; and
7. monitoring $N_2$ generation cell growth and $N_2O$ gas reduction.

TABLE 3 indicates the rate of $N_2O$ reduction as a function of the weight of (dry) cells in the culture and measure by millimole per mole per milligram of dry cells per hour.

TABLE 3

| | Rates of $N_2O$ Reduction (mM/M/mg/Hr) | |
|---|---|---|
| | With PFC | No PFC |
| 1st $N_2O$ Addition | 0.0112 | 0.0086 |
| 2nd $N_2O$ Addition | 0.0114 | 0.0067 |

This research demonstrates the feasibility and potential for using PFCs in applications involving industrial gases. The exposure of actively metabolizing bacteria to PFCs allowed for increased rates of $N_2O$ reduction in these nonoptimized batch culture experiments. Because metabolic rates were nearly increased by a factor of 2 with perfluorocarbons, increased reactor efficiency should translate to either decreased reactor size and reduced operational costs or increased gas through-put.

Studies of gas solubility of PFCs in liquid media were also conducted utilizing various gases and perfluorocarbons. Gases were injected into gas tight serum bottles containing microbiological media with and without the perfluorocarbons. Liquid content was 100 mL, headspace in bottles was 65 mL with a helium atmosphere. PFC concentrations was 15% (vol/vol). The results of these studies are shown in Table 4 where it can be seen that the gas solubility was increase in varying degrees with PFCs relative to controls.

TABLE 4

| | Percent Solubility in Microbiological Medium | | | |
|---|---|---|---|---|
| Gas | Control | PFC 40 | PFC 72 | PFC 77 |
| $CO_2$ | 80 | 85 | 82 | 85 |
| $N_2O$ | 27 | 59 | 55 | 56 |
| $CH_4$ | 3 | 7 | 24 | 11 |
| CO | 2 | 9 | 29 | 24 |

Several analyses were also conducted in order to determine the solubility of gasoline vapors in air tight bottles containing microbial media with and without PFCs. Results indicated that, relative to control, benzene and toluene are soluble in PFC 77 and PFC 72, and ethyl benzene and xylene are soluble in PFC 77 and PFC 40. (PFC 77 generically know as perfluorohexane, PFC 72 generically known as perfluourohexane and PFC 40 generically known as perfluorodecalin are tradenames of the Minnesota Mining and Manufacturing Company). Higher chain compounds demonstrate solubility in all PFCs tested. These results indicate the beneficial use of PFCs in microbial media to enhance the solubility of gases and gasoline vapors important for bioprocessing and bioremediation. It was observed that the bacterial contact with the PFCs was minimized due to the high density of the PFCs relative to that of water. Since enhanced mass transfer with PFCs occurs when they first contact the gases in the headspace and transfer the gases to bacteria, contact with the bacteria increases the mass transfer rate.

Table 5 shows a summary of the solubility of each gas in the PFC as well as the bacterial growth in the PFC and gas environment. The microorganisms used in the studies were specific for each compound so that microbial growth could be observed. For the hydrocarbon studies, the microorganisms used were a mixed culture from compost. Accordingly, the present invention can be used with any microorganism which is capable of the microbial utilization of the solubilized gas.

TABLE 5

| Gas | Increased Solubility in PFC | Bacterial Growth in PFC & Gas | Enhanced Degradation Rate with PFC |
|---|---|---|---|
| CO | + | + | |
| $CO_2$ | + | + | |
| $O_2$ | + | + | |
| $N_2O$ | + | + | + |
| NO | +. | + | + |
| $CH_4$ | + | + | |
| Benzene | + | + | + |
| Toluene | + | + | + |
| Ethylbenzene | + | + | + |
| Xylene | + | + | + |

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

I claim:

1. A method for anaerobic microbial utilization of industrial gas using perfluorocarbon (PFC) emulsions, the improved method comprising:
   a. providing a sterile PFC solution;
   b. mixing the PFC solution with an aqueous biological growth medium and a surfactant, the biological growth medium being suitable to support microbes capable of metabolically utilizing the industrial gas and the surfactant capable of being emulsified;
   c. emulsifying the biological growth medium, PFC solution, and surfactant mixture by circulation in a high-pressure emulsifier so that the PFc is in the distributed state throughout the emulsified biological growth medium;
   d. adding the emulsified biological growth medium, PFC solution, and surfactant mixture to a bioreactor containing microbes capable of metabolically utilizing the industrial gas;
   e. aseptically adding the industrial gas to the bioreactor containing emulsified growth medium, PFC solution, and surfactant mixture such that the industrial gas dissolves in the PFC solution at a higher concentration than in the growth medium, wherein the industrial gas is selected from the group consisting of nitrous oxide, nitric oxide, nitrogen dioxide, and carbon monoxide; and
   f. controlling a temperature and agitation rate of the growth medium, PFC solution and microbes within the bioreactor to maintain conditions sufficient for the microbes to utilize the industrial gas from the PFC solution, thereby increasing the utilization rate of the industrial gas by the microbes over the rate that would have been achieved without the PFC solution.

2. The method as recited in claim 1 wherein the PFC is selected from the group consisting of perfluorodecalin, perfluorohexane, perfluoropentane, perfluorobenzene, perfluorobutane, perfluoroheptane, perfluorooctane, perfluorononane, perfluorocyclobutane, perfluorocyclopentane, perfluorocyclohexane, perfluoromethylcyclohexane, perfluorodimethylcyclohexane, perfluoroethylcyclopentane, and perfluorotoluene, and mixtures thereof.

3. The method of claim 2 wherein the growth medium is a tryptic soy broth.

4. The method as recited in claim 3 wherein the microbes are *Pseudomonas denitrificans*.

5. The method of claim 1 wherein the surfactant is selected from the group consisting of sodium lauryl sulfate, monolaurate, monooleate, polyoxyethylene, polyoxypropylene, polyoxyethylenesorbitan, and block polymers.

6. The method of claim 1 wherein the emulsifier creates a PFC emulsion size of less than 100 nm in diameter.

7. A method for microbial utilization of hydrocarbon vapors using perfluorocarbon (PFC) emulsions, the method comprising:
   a. providing a sterile PFC solution;
   b. mixing the PFC solution with aqueous biological growth medium and a surfactant, the biological growth medium being suitable to support microbes capable of metabolically utilizing the hydrocarbon vapors and the surfactant capable of being emulsified;
   c. emulsifying the biological growth medium, PFC solution, and surfactant mixture by circulation in a high-pressure emulsifier so that the PFC is in the distributed state throughout the emulsified biological growth medium;
   d. adding the emulsified biological growth medium, PFC solution, and surfactant mixture to a bioreactor containing microbes capable of metabolically utilizing the hydrocarbon vapors;
   e. aseptically adding the hydrocarbon vapors to the bioreactor containing emulsified growth medium, PFC solution, and surfactant mixture such that the vapors dissolve in the PFC solution at a higher concentration than in the growth medium; and
   f. controlling a temperature and agitation rate of the growth medium, PFC solution and microbes within the bioreactor to maintain conditions sufficient for the microbes to utilize the vapor from the PFC solution, thereby increasing the utilization rate of the hydrocarbon vapors by the microbes over the rate that would have been achieve without the PFC Solution.

8. The method as recited in claim 7 wherein the PFC is selected from the group consisting of perfluorodecalin, perfluorohexane, perfluoropentane, perfluorobenzene, perfluorobutane, perfluoroheptane, perfluorooctane, perfluorononane, perfluorocyclobutane, perfluorocyclopentane, perfluorocyclohexane, perfluoromethylcyclohexane, perfluorodimethylcyclohexane, perfluoroethylcyclopentane, and perfluorotoluene, and mixtures thereof.

9. The method of claim 8 wherein the growth medium is a tryptic soy broth.

10. The method as recited in claim 7 wherein the hydrocarbon vapor is selected from the group consisting of methane, hexane, butane, propane, phenols and chlorinated hydrocarbons.

11. The method of claim 10 wherein the surfactant is selected from the group consisting of sodium lauryl sulfate, monolaurate, monooleate, polyoxyethylene, polyoxypropylene, polyoxyethylene-sorbitan, and block polymers.

12. The method of claim 7 wherein the emulsifier creates a PFC emulsion size of less than 100 nm in diameter.

13. A method for microbial utilization of volatile organic compound vapors using perfluorocarbon (PFC) emulsions, the improved method comprising:
   a. providing a sterile PFC solution;
   b. mixing the PFC solution with an aqueous biological growth medium and a surfactant, the biological growth medium being suitable to support microbes capable of metabolically utilizing the volatile organic compound vapors and the surfactant capable of being emulsified;
   c. emulsifying the biological growth medium, PFC solution, and surfactant mixture by circulation in a high-pressure emulsifier so that the PFC is in the distributed state throughout the emulsified biological growth medium;
   d. adding the emulsified biological growth medium, PFC solution, and surfactant mixture to a bioreactor containing microbes capable of metabolically utilizing the volatile organic compound vapors;
   e. aseptically adding the volatile organic compound vapors to the bioreactor containing emulsified growth medium, PFC solution, and surfactant mixture such that the vapors dissolve in the PFC solution at a higher concentration than in the growth medium; and f. controlling a temperature and agitation rate of the growth medium, PFC solution and microbes within the bioreactor to maintain conditions sufficient for the microbes to utilize the vapors from the PFC solution, thereby increasing the utilization rate of the volatile organic compound vapors by the microbes over the rate that would have been achieved without the PFC solution.

14. The method as recited in claim 13 wherein the PFC is selected from the group consisting of perfluorodecalin, perfluorohexane, perfluoropentane, perfluorobenzene, perfluorobutane, perfluoroheptane, perfluorooctane, perfluorononane, perfluorocyclobutane, perfluorocyclopentane, perfluorocyclohexane, perfluoromethylcyclohexane, perfluorodimethylcyclohexane, perfluoroethylcyclopentane, and perfluorotoluene, and mixtures thereof.

15. The method of claim 14 wherein the growth medium is a tryptic soy broth.

16. The method as recited in claim 13 wherein the volatile organic compound is selected from the group consisting of benzene, toluene, ethylbenzene, and xylene.

17. The method of claim 13 wherein the surfactant is selected from the group consisting of sodium lauryl sulfate, monolaurate, monooleate, polyoxyethylene, polyoxypropylene, polyoxyethylene-sorbitan, and block polymers.

18. The method of claim 13 wherein the emulsifier creates a PFC emulsion size of less than 100 nm in diameter.

* * * * *